US00PP07886P

United States Patent [19]

van Andel

[11] Patent Number: Plant 7,886

[45] Date of Patent: Jun. 16, 1992

[54] ALSTROEMERIA NAMED STALIBLA

[75] Inventor: Jacob van Andel, Aalsmeer, Netherlands

[73] Assignee: Van Staaveren B.V., Aalsmeer, Netherlands

[21] Appl. No.: 560,097

[22] Filed: Jul. 30, 1990

[51] Int. Cl.[5] ..... A01H 5/00

[52] U.S. Cl. ..... Plt./68

[58] Field of Search ..... Plt./68, 87.1

[56] References Cited

U.S. PATENT DOCUMENTS

P.P. 4,930 11/1982 van Andel ..... Plt. 68

P.P. 7,078 12/1989 Goemans ..... Plt. 68

*Primary Examiner*—Howard J. Locker

[57] ABSTRACT

A new and distinctive Alstromeria cultivar particularly distinguished by the almost white outer petals of a very large flower especially characterized by its long elliptically shaped inner petals which terminate in a distinctive aristate tip and have a lemon yellow coloration for about two-thirds of its length from the base end, the outer portion being of the almost white color of the outer petals. The relatively narrow inside petals are also distinguished by short dark brown pencil stripes which extend longitudinally from the petal base to its tip. This plant being further characterized by its profuse year around blooming habit on an upright fast growing bush of which the cane length is about 180 cm.

1 Drawing Sheet

BACKGROUND OF THE NEW PLANT

This Alstroemeria cultivar originated as a sport of the variety Stalbel, U.S. Plant Pat. No. 6,193 grown at Aalsmeer, The Netherlands, discovered by me at Aalsmeer in 1984 and selected for propagation and test in the course of my objective of developing new colors in the 'Stalbel' family. Propagation of this sport was done under my direction by cuttings of roots with such success that propagation by dividing rhizomes was carried on through several successive generations which demonstrated clearly that the novel characteristics of the discovered sport would be retained from generation to generation and appear to be firmly fixed.

DESCRIPTION OF THE DRAWING

The accompanying color photographic drawing shows typical inflorescence, bud, and foliage characteristics of 'Stalibla', with colors being as nearly true as possible to obtain by conventional photographic procedures.

DESCRIPTION OF THE NEW PLANT

The following is a detailed description of my new Alstroemeria cultivar as observed at Aalsmeer, with color designations according to the R.H.S. Colour Chart of The Royal Horticultural Society of London, England.

THE PLANT

Origin: Sport.

Parentage: The variety 'Stalbel', U.S. Plant Pat. No. 6,193.

Classification:

*Botanic.*—Alstroemeria hybrid.

*Commercial.*—Alstroemeria.

Form: A tall, slender, flowering stalk with flower bearing branches at its top.

Height: About 180 cm.

Growth rate: Vigorous, fast and upright.

Root stock rhizomes: Bearing many buds during the year from which the flower stalks grow in various stages of development during the course of the year.

Branching character: Each flower stalk branches at the top to produce seven or more flower bearing stems.

Foliage:

*Quantity.*—Medium.

*Number of leaves.*—Varying from season to season through the year.

*Size of leaf.*—Large.

*Leaf shape.*—Elliptic with entire margins.

*Texture.*—Soft.

*Color.*—Upper side — Middle Green. Under side — Grey Green.

Rhizomes:

*Size.*—Varying from season to season.

*White.*—White.

THE BUD

Size: Large.

*Diameter.*—About 2 cm.

*Length.*—About 4 cm.

Form: Pear-shaped.

Opening rate: The bud opens slowly.

THE INFLORESCENCE

Blooming habit: Continuous and profusely the year around.

Flower size: Very large.

*Diameter.*—About 7 cm.

*Depth.*—About 6 cm.

Borne: Singly.

Petalage:

*Number of petals.*—6.

*Arrangement.*—Imbricated with two concentric circles each of three petals.

*Texture.*—Soft.

*Appearance.*—Satiny.

*Color.*—Outer petals — body and base, RHS 158-C, the year around; base, 158-C the year around, reverse side, 158-C with 66-C in Springtime and 66-D during the balance of the year. Outer petals have no brown striping, or at the very most, an occasional single short brown pencil stripe, located in the central area thereof. Inside petals — about two-thirds of the inside portion of the body 13-B with the upper most portion 158-C and reverse side outer portion 158-C and the inner portion 12-C, the year around. Inside petals have numerous short dark brown pencil stripes which extend longitudinally from petal base to tip.

Peduncle:

*Length.*—About 2 cm.

*Color.*—Light green.

*Character.*—Strong and upright.

Discoloration after full bloom: The flower becomes lighter to 158-D.

Effect of weather: None.

Persistence: The flowers hang on and dry.

Fragrance: None.

Lasting quality:

*On plant.*—About 20 days.

*As cut flower.*—About 14 days.

THE REPRODUCTIVE ORGANS

Stamens:

*Number.*—Six.

*Arrangement.*—One opposite each petal.

*Anthers.*—Size: About 10 mm. Color: Green/Yellow.

*Filaments.*—Length: About 45 mm. Color: Salmon.

*Pollen.*—Color: Yellow.

Pistils:

*Number.*—One.

Style:

*Length.*—About 35 mm.

*Color.*—Salmon.

Stigma:

*Color.*—Salmon.

This plant most nearly resembles its parent, Stalbel, but is distinguished therefrom particularly by the flower color.

I claim:

1. The new and distinctive Alstroemeria cultivar, substantially as herein shown and described, characterized by its almost white wide outer petals and distinguished by the lemon yellow coloring of the inner two-thirds of the inner petal length and the dark pencil stripes which extend from end to end of the inner petal body.

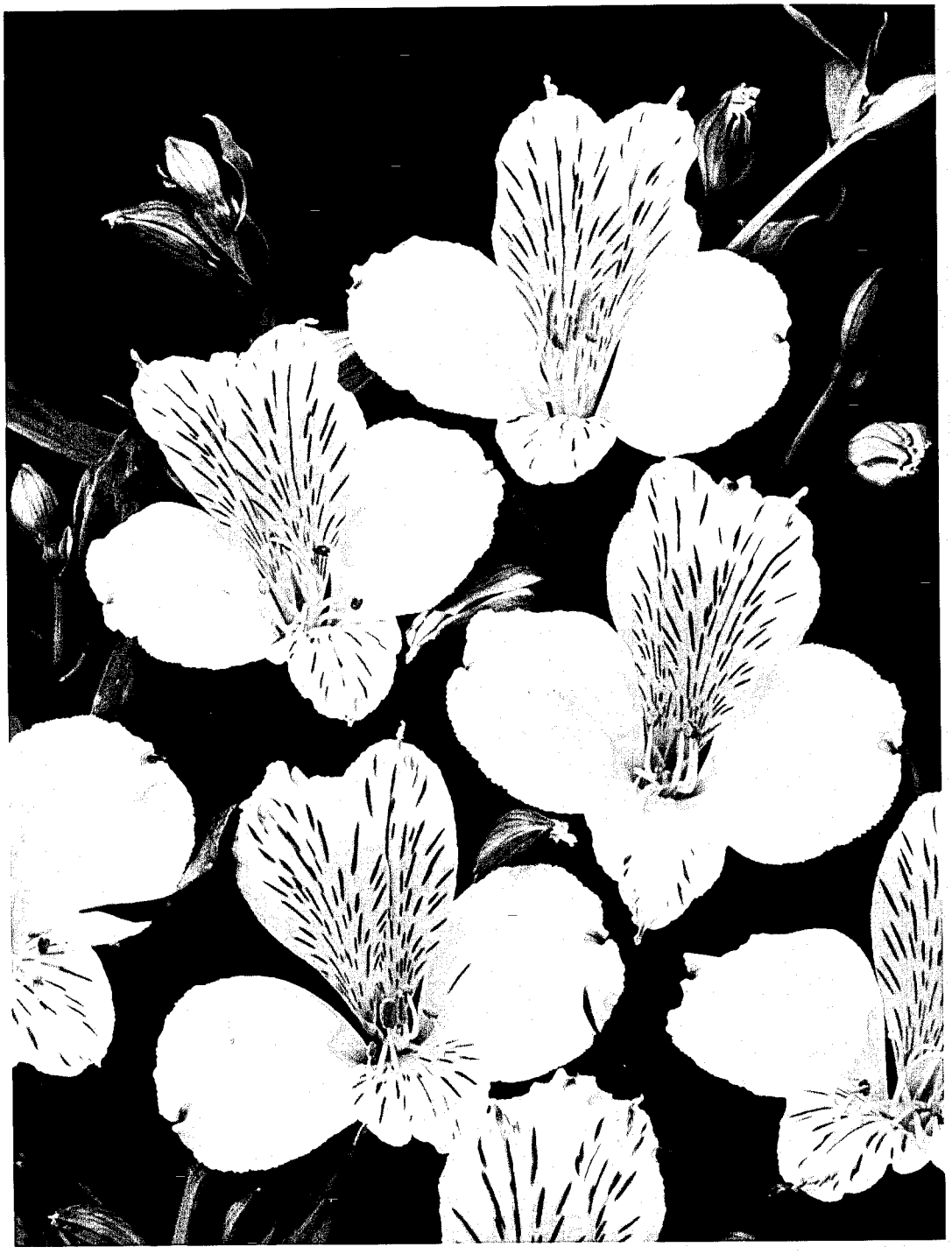

* * * * *